(12) United States Patent
Maeda et al.

(10) Patent No.: US 7,556,829 B2
(45) Date of Patent: Jul. 7, 2009

(54) **METHOD FOR PRODUCING *MALLOTUS PHILIPPINENSIS* DYE COMPOSITION AND THE COMPOSITION**

(75) Inventors: Mitsuru Maeda, Otsu (JP); Harukazu Fukami, Kyoto (JP); Koshi Namikawa, Hirakata (JP)

(73) Assignee: Suntory Holdings Limited, Osaka (JP)

( * ) Notice: Subject to any disclaimer, the term of this patent is extended or adjusted under 35 U.S.C. 154(b) by 161 days.

(21) Appl. No.: 10/592,426

(22) PCT Filed: Mar. 11, 2005

(86) PCT No.: PCT/JP2005/004325

§ 371 (c)(1),
(2), (4) Date: Sep. 11, 2006

(87) PCT Pub. No.: WO2005/087871

PCT Pub. Date: Sep. 22, 2005

(65) Prior Publication Data

US 2007/0207219 A1    Sep. 6, 2007

(30) Foreign Application Priority Data

Mar. 12, 2004    (JP) .............................. 2004-070796

(51) Int. Cl.
*A61K 36/00*    (2006.01)
(52) U.S. Cl. ..................................................... 424/725
(58) Field of Classification Search ........................ None
See application file for complete search history.

(56) References Cited

U.S. PATENT DOCUMENTS

2003/0138939 A1* 7/2003 Vodyanoy et al. ........... 435/260

2005/0158435 A1    7/2005 Abe et al.

FOREIGN PATENT DOCUMENTS

| JP | 47-43268 | 12/1972 |
|---|---|---|
| JP | 1-132505 | 5/1989 |
| JP | 2003-55369 | 2/2003 |
| JP | 2003-146837 | 5/2003 |
| WO | 03/075686 | 9/2003 |

OTHER PUBLICATIONS translation of Masazumi (JP 2003-146837)—2003.*
Nankodo, "Pharmacognosy," 1966 [in Japanese].
H. Jayasuriya et al., "Antimicrobial and Cytotoxic Activity of Rottlerin-Type Compounds From *Hypericum drummondii*," *Journal of Natural Products*, 1989, vol. 52(2), pp. 325-331.
International Search Report dated May 27, 2003 from PCT/JP03/02850.
Nankodo, "Pharmacognosy," 1966, pp. 169-170 (English-language translation).

* cited by examiner

*Primary Examiner*—Susan C Hoffman
(74) *Attorney, Agent, or Firm*—Drinker Biddle & Reath LLP

(57) ABSTRACT

An object of the present invention is to provide a *Mallotus philippinensis* extract containing readily water soluble rottlerin. A further object of the present invention is to improve convenience at production steps in a method for producing such an extract, by avoiding the staining of filters and/or pipes during extraction and filtration to reduce washing costs, or by facilitating the introduction of freeze drying and so on. When a dye extract is extracted with water and alcohol from a *Mallotus philippinensis* plant body, the addition of a base component drastically improves the water solubility of the *Mallotus philippinensis* extract. This improves extraction rates of rottlerin, facilitates washing in the production and the pulverization of the extract, and also improves the water solubility of the obtained extract.

16 Claims, 2 Drawing Sheets

METHOD FOR PRODUCING *MALLOTUS PHILIPPINENSIS* DYE COMPOSITION AND THE COMPOSITION

TECHNICAL FIELD

The present invention relates to a method for extracting a *Mallotus philippinensis* dye, particularly a dye derived from its pericarp, which is typified by rottlerin.

BACKGROUND ART

Red powders called kamala, which are obtained from minute glands and hairs on the skins of fruits of *Mallotus philippinensis* produced in India, Philippines, Southeast Asia, and Australia, are used as a taeniafuge or dyestuff and said to contain rottlerin, which is a phloroglucinol derivative, as an active ingredient (Pharmacognosy, Nankodo, 1966).

As to the extraction of a dye from *Mallotus philippinensis*, a method of extraction by heating with 100% ethyl alcohol is disclosed in Japanese Patent Laid-Open No. S47-43268, and a method of extraction with water, a hydrophilic organic solvent or a mixture solution thereof at room temperature or at a solvent boiling point or lower is disclosed in Japanese Patent Laid-Open No. 2003-146837. Further, Japanese Patent Laid-Open No. 2003-55369 discloses that a phloroglucinol derivative was purified by performing water and/or organic solvent extraction and further performing n-hexane extraction, Sephadex LH-20 column chromatography and silica gel chromatography. Drummondins, which are phloroglucinol derivatives having antimicrobial activity to Gram-positive bacteria *Staphylococcus aureus* and *Bacillus subtilis*, have been isolated from *Hypericum drummondii* belonging to the family of Guttiferae (Journal of Natural Products, Vol. 52, No. 2, p. 325-331, 1989). These substances have also been purified from hexane extracts of the leaves and stems of the plant.

According to these disclosed results, kamala dyes or phloroglucinol derivatives are extracted with 100% ethyl alcohol or with n-hexane, a low-polarity solvent. Thus, a dye component rottlerin is rich in lipid solubility, and was difficult to apply to drinks since an emulsifier or the like needs to be used to disperse the dye in the drinks. At the site of producing the dye component, the component causes the staining of pipes therewith, the adsorption thereof into filters, and so on, due to its high lipid solubility; and therefore requires undue labor for washing.

[Patent Document 1]: Japanese Patent Laid-Open No. S47-43268

[Patent Document 2]: Japanese Patent Laid-Open No. 2003-146837

[Patent Document 3]: Japanese Patent Laid-Open No. 2003-55369

[Non-Patent Document 1]: "Pharmacognosy", Nankodo, p. 169, 1966

[Non-Patent Document 2]: Journal of Natural Products, Vol. 52, No. 2, p. 325-331, 1989

DISCLOSURE OF THE INVENTION

Problems to be Solved by the Invention

The first object of the present invention is to provide a *Mallotus philippinensis* dye composition containing rottlerin enhanced in water solubility as a main dye component, and a method for producing the same.

The second object of the present invention is to improve convenience at production steps in the production of the *Mallotus philippinensis* dye composition containing rottlerin as a main dye component, by avoiding the staining of filters or pipes during the extraction and filtration of *Mallotus philippinensis* to reduce washing costs, and/or by enhancing the water solubility of the extracted component of *Mallotus philippinensis* to facilitate the introduction of freeze drying instead of vacuum drying.

Means for Solving the Problems

The present inventors have completed the present invention by finding that when a dye extract is extracted with an aqueous alcohol solvent from a *Mallotus philippinensis* plant body, the presence of a base component drastically improves the solubility of *Mallotus philippinensis* dye components in the solvent and facilitates the washing of equipment used in the production and the pulverization of the extract, and by finding that the dye, particularly rottlerin, contained in the extract is easily dissolved in water.

Hereinafter, the present invention will be described in detail.

The present invention relates to a method for producing a *Mallotus philippinensis* dye composition characterized by extracting a dye component from a *Mallotus philippinensis* plant body in the presence of a base component. A solvent used in the extraction is preferably an alcohol-containing aqueous solvent.

To be more specific, the present invention relates to a method for producing a substantially water-soluble *Mallotus philippinensis* dye composition comprising the following steps of:

i) preparing a *Mallotus philippinensis* plant body;

ii) preparing an aqueous solvent containing $C_1$ to $C_3$ alcohol, preferably $C_2$ alcohol;

iii) mixing a base component, the *Mallotus philippinensis* plant body, and the alcohol-containing aqueous solvent in any order to obtain a mixture thereof;

iv) for the mixture obtained in the step iii), extracting a dye component with the alcohol-containing aqueous solvent from the *Mallotus philippinensis* plant body to obtain an extracted solution; and v) if necessary, concentrating and/or drying the extracted solution obtained in the step iv) to obtain a concentrated or dried extract.

The term "*Mallotus philippinensis* plant body" used herein refers to, but not limited to, leaves, flowers, roots, bark, branches, fruits, pericarp, and glandular hairs constituting *Mallotus philippinensis*. The *Mallotus philippinensis* plant body is preferably kamala, which is obtained by drying the glandular hairs.

The "*Mallotus philippinensis* dye composition" in the present invention refers to a composition which is obtained from the *Mallotus philippinensis* plant body, and comprises rottlerin.

The solvent used in extraction in the method of the present invention comprises water and alcohol. Water which is available in the present invention may be water used in the production of foods and drinks, for example deionized water and distilled water. Alcohol which is available in the present invention is $C_1$ to $C_3$ alcohol, preferably ethyl alcohol. An alcohol concentration in the solvent is preferably 30 to 90% by volume, more preferably 30 to 70% by volume, even more preferably 50% by volume.

In the method of the present invention, the base component used in extraction of a dye component from the *Mallotus philippinensis* plant is, in the view of situations where the extract is added to foods, preferably, but is not particularly limited to, ammonium carbonate, potassium carbonate, sodium carbonate (sal soda), sodium bicarbonate (baking soda), tripotassium phosphate (potassium phosphate, tribasic), diammonium hydrogen phosphate, dipotassium hydrogen phosphate, disodium hydrogen phosphate, trisodium phosphate, potassium hydroxide, or sodium hydroxide, which is described in the list of food additives. Two or more of them may be mixed for use.

In the production method of the present invention, the base component is mixed with the *Mallotus philippinensis* plant body and the alcohol-containing aqueous solvent in any order. For example, the base component may be mixed with the solvent and then with the *Mallotus philippinensis* plant body, or may be mixed with in advance with the plant body and then with the solvent. Alternatively, the base component may also be mixed with a mixture obtained by mixing the plant body and the solvent.

The amount of the base used may appropriately be determined by those skilled in the art. As a guideline, the pH of the solvent is controlled to 7.0 or higher, preferably 7.0 to 11.0, particularly preferably 7.0 to 9.0 (normal temperature (15 to 25° C.) or ambient temperature), before, during and after extraction. For this purpose, for example sodium bicarbonate, sodium carbonate, or trisodium phosphate is conveniently used. In this context, the amount of the base component used is 10 to 300% by weight, particularly preferably 10 to 30% by weight, with respect to the amount of the raw material. To control the pH exhibited before and after extraction, an appropriate buffer may further be added in addition to the base component, or alternatively, an additional base may be added during extraction to control the pH. The buffer used includes, but not limited to, Atkins & Pantin's sodium carbonate/boric acid mixture solutions, sodium tetraborate/sodium hydroxide buffer solutions, boric acid/potassium chloride/sodium hydroxide buffer solutions, and glycine/sodium hydroxide buffer solutions.

Concrete extraction treatment procedures and apparatuses for performing the steps i) to v) are not particularly limited as long as they allow for the elution of a soluble dye component contained in *Mallotus philippinensis* into the extraction solvent. For example, the steps iii) and iv) are performed by uniformly mixing the *Mallotus philippinensis* plant body and the base component in advance, charging the mixture into a treatment bath filled with an extraction solvent, and letting it stand for usually 1 to 3 hours, if necessary with occasional stirring, to elute a soluble component. The amount of the solvent used in extraction, for example the amount of the solvent present in the extraction system at the step iv), is usually 5 to 40 times by weight, preferably 5 to 20 times by weight, larger than that of the raw material for the extraction. The temperature of the solvent in extraction is normal temperature to heating reflux temperature (15 to 90° C.), preferably 50 to 80° C. If necessary, solid matter is removed from the obtained extracted solution. For this purpose, a known method such as filtration may be used. The extracted solution thus obtained may directly be used as the composition of the present invention or, if necessary, is concentrated and/or dried according to the step v) to obtain the composition of the present invention. The concentration can be performed under a normal pressure or a reduced pressure. Conditions such as temperature and time in this concentration procedure are appropriately selected so as not to degrade the dye component. The exsiccation or drying is performed by ordinary means, for example freeze drying, drying under reduced pressure, or circulation drying. Conditions such as temperature and time in this procedure are also appropriately selected so as not to degrade the dye component.

The *Mallotus philippinensis* dye composition thus obtained possibly has unique bitter tastes and smells and may therefore by purified, for example by washing the extracted solution thereof or the concentrated or dried product of the extracted solution thereof, with hexane. Alternatively, for this purpose, the *Mallotus philippinensis* plant body may be washed in advance with hexane or steamed in water vapor before the extraction procedures.

The composition produced by the method of the present invention is advantageous in that it is substantially water-soluble and is easily pulverized. The phrase "substantially water-soluble" used in the present invention means being water-soluble at a practical level. For example, when rottlerin is "substantially water-soluble", the water solubility of rottlerin is 250 µg/mL or higher, preferably 1,500 µg/mL or higher, more preferably 5,500 µg/mL or higher, even more preferably 12,000 µg/mL or higher. Water solubility may be measured by any method routinely used, and may be measured, for example as described in Example 4 below, by adding a sample to water (preferably at room temperature (1 to 30° C.)) and stirring the mixture to measure a rottlerin concentration in the supernatant.

The dye composition of the present invention can be mixed as a dyestuff, a coloring agent, a preservative agent (e.g., a preservative, a germicide, and a keeping quality-improving agent), a taeniafuge, a flavor, and so on, in foods and drinks or cosmetics. The types of the foods and drinks in which the *Mallotus philippinensis* dye composition of the present invention can be mixed are not particularly limited, and concrete examples thereof include: drinks such as soft drinks, carbonated drinks, energy drinks, fruit drinks, lactic fermenting beverages, and soups (including concentrated undiluted liquids and powders for preparation of these drinks); frozen desserts such as ice lollies, ice creams, soft serve ice creams, ice sherbets, ice shavings, and water ice; confectionery such as gums, chocolates, wheat-gluten, chewing gums, gummy candies, candies, tablets, snacks, biscuits, jam, creams, and bakegoods; desserts such as jelly, yogurt, custard pudding and bavarois; noodles such as Japanese wheat noodles, buck-wheat noodles, Japanese vermicelli, cold wheat noodles (hiyamugi), spaghetti, macaroni, rice vermicelli, bean-starch vermicelli, jiao-zi skins, Shao-mais skins, won-ton, Chinese noodles, and instant noodles; marine or livestock processed products such as hams, sausages, fish sausages (chikuwa), steamed fish pastes (kamaboko), fish minced and steamed (Hanppen), and fried fish balls (Satsuma-age); dairy products such as processed milk and fermented milk; fat and oil and fat and oil processed foods such as cooking oils, frying oils, margarine, mayonnaise, shortening, whipped creams, and dressings; seasonings such as sauce and baste; pickles such as pickled gingers, pickled plums, "Fukujin-zuke" (vegetables pickled in soy sauce), and "Shiba-zuke" (pickled cucumber); and stews, salads, and daily dishes. For example, the dye composition of the present invention can be used as a preservative in soft drinks such as tea. Moreover, examples of the types of cosmetics in which the *Mallotus philippinensis* dye composition can be mixed include cosmetics for face, skin, and head hair, fragrance products such as perfumes and colognes, and oral products such as mouth washes and dentifrices.

Advantage of the Invention

According to the present invention, a dye composition containing an easily water soluble *Mallotus philippinensis* dye, particularly rottlerin, as an active ingredient is provided. The dye composition of the present invention is useful for the applications to foods and drinks that encompass drinks such as soft drinks, carbonated drinks, energy drinks, fruit drinks, and lactic fermenting beverages (including concentrated undiluted liquids and powders for preparation of these drinks).

According to the production method of the present invention, a high dye extraction rate is achieved by use of an aqueous alcohol system having an alcohol concentration lower than ever before.

An extracted solution obtained by the present invention has the *Mallotus philippinensis* dye, particularly rottlerin, enhanced in water solubility, and therefore facilitates the introduction of freeze drying. Thus, the production method of the present invention improves the convenience of work in the method for producing an extract.

Moreover, the production method of the present invention facilitates the washing of manufacturing lines and containers, reduces the amount of the solvent required for the washing, and reduces washing time required for the washing, by virtue of the enhanced solubility of the dye component in the solvent. Furthermore, the method of the present invention facilitates the pulverization of the obtained dye. Therefore, the present invention is useful for reducing costs in the dye production.

BRIEF DESCRIPTION OF THE DRAWINGS

FIG. 1 is a scatter diagram showing the relationship between a chromatogram peak area and a rottlerin concentration;

FIG. 2 is a comparative bar graph showing an effect of $NaHCO_3$ added to 50% EtOH;

FIG. 3 is a comparative bar graph showing an effect of $NaHCO_3$ added to 90% EtOH; and

FIG. 4 is a scatter diagram showing the relationship between the pH of a solution after extraction treatment and a rottlerin extraction rate.

BEST MODE FOR CARRYING OUT THE INVENTION

Hereinafter, the present invention will be described more fully with reference to Examples. However, the scope of the present invention is not intended to be limited to these Examples by any means.

In each of the Examples below, ethanol concentration is indicated in % by volume, and the amount of a base component such as sodium bicarbonate is indicated in % by weight with respect to that of a raw material, unless otherwise specified.

EXAMPLE 1

HPLC Analysis of a Dye Component of *Mallotus philippinensis*, Rottlerin

When rottlerin (manufactured by Sigma) was purchased and measured for its absorption maximum wavelengths in a solution of 100% acetonitrile ($CH_3CN$)-0.05% trifluoroacetic acid (TFA) (100% $CH_3CN$ containing 0.05% of TFA), which is an HPLC mobile phase, the maximum wavelengths were 288.0 and 350.0 nm. The wavelength of 350 nm, which was distinguished better from the absorption wavelengths of impurities, was used as a detection wavelength, to set HPLC conditions as follows:

HPLC system: LC-10Ai (manufactured by Shimadzu Corporation) Column: Develosil C30-UG-5 (3.0×150 mm, manufactured by Nomura Chemical Co., Ltd)

Figure 1:
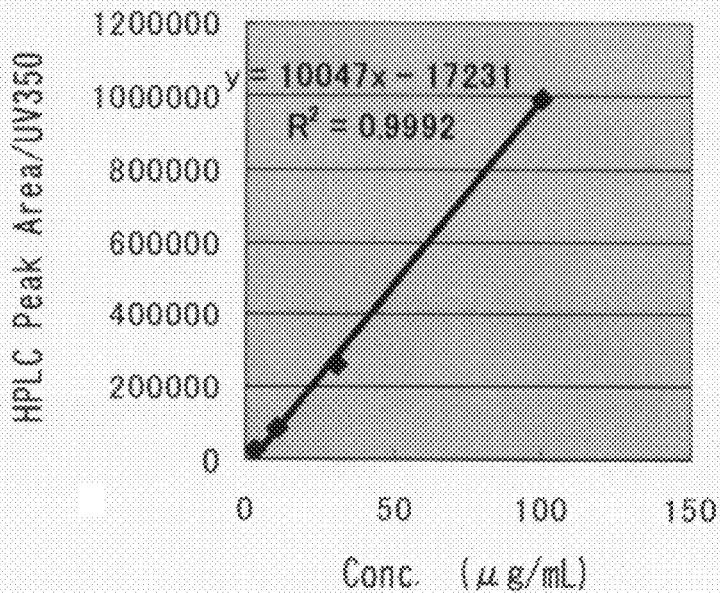
[FIG. 1]

Column temperature: 40° C.
Mobile phase: 80% $CH_3CN$-0.05% TFA
Flow rate: 0.4 mL/min
Detection wavelength: 350 nm
Injection amount: 5 µL
Retention time: 12.7 min Rottlerin was dissolved in 90% ethanol and prepared into 3, 10, 30, and 100 µg/mL solutions thereof to create a calibration curve. The results are shown in FIG. 1. The relationship between the obtained chromatogram peak areas and the concentration was indicated by a regression line through the origin. The formula for the line was {Concentration (µg/mL)=(Peak Area+17231)/10047}. The correlation coefficient index $R^2$ was 0.9992.

EXAMPLE 2

Effect of Sodium Bicarbonate Addition During Extraction

To 500 mg of kamala powders (hereinafter, referred to as the raw material), which are glandular hairs of *Mallotus philippinensis*, 10 mL (20 times by volume) of 50 or 90% ethanol was added and heated at 80° C. for 1 hour to perform extraction. The extracted solutions were centrifuged to obtain their respective supernatants, and the supernatants were brought up to 20 mL with 90% ethanol, and a portion thereof was further diluted with 90% ethanol to perform HPLC analysis according to Example 1. As a result, a rottlerin concentration in the sample extracted with 90% ethanol was calculated to be 4.846 mg/mL. When the value was converted to the amount of rottlerin extracted from 500 mg of the raw material, the converted value was 96.9 mg (extraction rate: 19.4%). By contrast, the 50% ethanol extraction yielded 5.0 mg of rottlerin (extraction rate: 1%), which was approximately one twentieth of the 90% ethanol extract.

Figure 2:
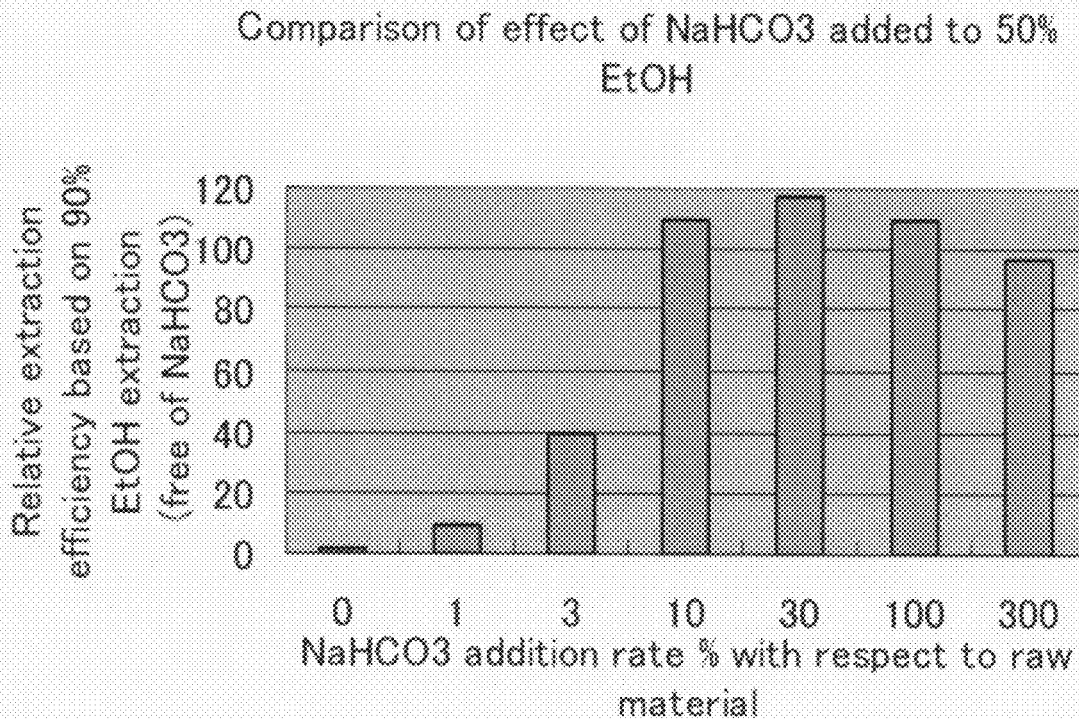
[FIG. 2]

Next, during the extraction with 50% ethanol (20 volumes of the law material), 1% (i.e., 5 mg), 3% (i.e., 15 mg), 10% (i.e., 50 mg), 30% (i.e., 150 mg), 100% (i.e., 500 mg), or 300% (i.e., 1500 mg) of sodium bicarbonate was added to the eluent, followed by the same treatment as that described above. The amount and extraction rate of rottlerin in the obtained extracted samples were calculated. This extraction rate was compared with the rottlerin extraction rate described above (19.4%) which was accomplished when extracting with 90% ethanol free of sodium bicarbonate. In this Example, this 90% extraction with ethanol free of sodium bicarbonate was called a control (see FIG. 3 below), and its extraction rate was used as a reference to determine relative extraction efficiencies of each of the other extraction experiments. The results are shown in FIG. 2.

When the extraction procedures were performed with the alcohol concentration of 50% without the addition of sodium bicarbonate (i.e., addition rate: 0%), the relative extraction efficiency thereof was as few as 5.2%. By contrast, when sodium bicarbonate ($NaHCO_3$) was added at a concentration of 10% or higher with respect to that of the raw material, the extraction efficiency thereof was drastically improved. Specifically, the addition of 10% sodium bicarbonate improved the extraction efficiency by 21.2 times, the addition of 30% sodium bicarbonate improved the extraction efficiency by 22.7 times, the addition of 100% sodium bicarbonate improved the extraction efficiency by 21.2 times, and the addition of 300% sodium bicarbonate improved the extraction efficiency by 18.8 times. The relative extraction efficiency for the 300% sodium bicarbonate addition was 96.9% and was shown to be almost the same as the extraction rate of the control section. On the other hand, when the sodium bicarbonate addition rate exceeds 30%, white precipitates that seemed to be undissolved sodium bicarbonate coexisted in residues of extracted raw material.

Figure 3:
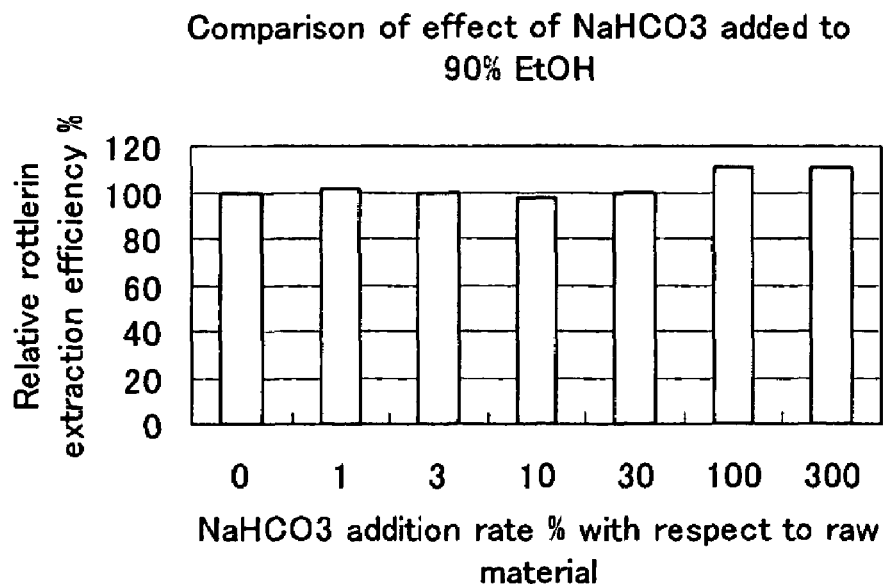
[FIG. 3]

Similarly, during the 90% ethanol extraction, 1%, 3%, 10%, 30%, 100%, or 300% sodium bicarbonate was added to the ethanol, and the extraction rate thereof was compared with that of the control. The results are shown in FIG. 3. High relative extraction efficiencies were observed in all the sodium bicarbonate addition rates.

As a result, conventional extraction methods, which did not use a base component, significantly reduced extraction efficiencies when decreasing an alcohol concentration from 90% to 50%, whereas the present invention, wherein a base was added, was shown to improve extraction efficiencies.

EXAMPLE 3

Efficiency of Extraction with Sodium Bicarbonate Addition

To 50 g of the raw material, 5 g (10% with respect to the raw material) of sodium bicarbonate was added and made uniform. The mixture was supplemented with 1 L of 50% ethanol and heated at 80° C. for 1 hour. After cooling to room temperature, a filtrate obtained by natural filtration was concentrated under a reduced pressure at 40° C. or lower to remove the alcohol, followed by freeze drying to obtain 24 g of a powder (hereinafter, referred to as powder A). By contrast, the same treatment was performed with 90% ethanol without the addition of sodium bicarbonate to obtain 15.8 g of a powder (hereinafter, referred to as powder B). When a rottlerin content in the extracted powder A and B was calculated according to Example 1, it was 23.5% in the powder A and 29.5% in the powder B. In consideration of the weight of powder and the rottlerin contents together, the extraction with the 10% sodium bicarbonate-supplemented 50% ethanol yielded 5.64 g of rottlerin, whereas the extraction with the sodium bicarbonate-free 90% ethanol yielded only 4.66 g of rottlerin. As a result, the extraction with the addition of sodium bicarbonate increased the amount of rottlerin collected to 1.2 times higher than that of the sodium bicarbonate-free extraction.

EXAMPLE 4

Comparison of Water Solubility

Water solubility was examined by the following method: an extracted solution obtained by extraction of the raw material with 50% or 90% ethanol supplemented with 10% or 30% sodium bicarbonate was dried to obtain a dried product, approximately 0.2 g each of which was added 4 mL (i.e., 20 times by volume) of distilled water, then stirred with a vortex mixer, and sonicated for 1 minute, followed by centrifugation to collect supernatants. Millipore filter unit MILLEX (registered trademark)-HV (0.45 μm) was used to obtain microfiltrates. A rottlerin concentration therein was determined by the method of Example 1. As a control, 90% ethanol free of sodium bicarbonate was used to perform the same procedures. The results are shown in Table 1.

TABLE 1

| Amount of sodium bicarbonate added with respect to raw material (% by weight) | Ethanol concentration (% by volume) | Rottlerin concentration in supernatant (μg/mL) | Relative solubility ratio |
| --- | --- | --- | --- |
| 10 | 50 | 12,750 | 196 |
| 30 | 50 | 5,681 | 89 |
| 10 | 90 | 1,576 | 25 |

TABLE 1-continued

| Amount of sodium bicarbonate added with respect to raw material (% by weight) | Ethanol concentration (% by volume) | Rottlerin concentration in supernatant (μg/mL) | Relative solubility ratio |
| --- | --- | --- | --- |
| 30 | 90 | 274 | 4 |
| 0 (Control) | 90 | 64 | 1 |

Explanations for Table 1: when the solubility of rottlerin contained in the sodium bicarbonate-free 90% ethanol extract (control) was defined as 1, relative solubility ratio based on the control was increased to 25 for the 10% sodium bicarbonate-supplemented 90% ethanol extract, and 196 for the 10% sodium bicarbonate-supplemented 50% ethanol extract. Specifically, the sodium bicarbonate-supplemented extract was significantly improved in water solubility as compared with the sodium bicarbonate-free extract. The 50% ethanol extract had much more excellent solubility than that of the 90% ethanol extract.

EXAMPLE 5

Study of Extraction Temperature

To the raw material, sodium bicarbonate was added at a concentration of 10% with respect to the raw material, and an extraction temperature was set to 26° C. to measure the amount of rottlerin extracted after 3 days or 7 days according to the method of Example 2. An ethanol concentration was adjusted to 50% or 90%. As a result, 15.5% or higher extraction rates were obtained in all the cases. Considering that the extraction rates in the extraction treatments at 80° C. for 1 hour with addition of 10% sodium bicarbonate were approximately 19% for all the alcohol concentrations as shown in Example 2, 80% or more of the extract rate was collected at normal temperature for 3 days.

TABLE 2

| Ethanol concentration (% by volume) | Extraction term (days) | Rottlerin extraction rate % |
| --- | --- | --- |
| 50 | 3 | 15.6 |
| 50 | 7 | 15.5 |
| 90 | 3 | 19.2 |
| 90 | 7 | 17.6 |

EXAMPLE 6

Study of Alcohol Concentration During Extraction

To the raw material, 10% or 100% sodium bicarbonate was added, and an ethanol concentration was set to 0% (i.e., distilled water), 30%, or 50% to measure the amount of rottlerin extracted by treatments at 80° C. for 1 hour, according to the method of Example 2. The results are shown in Table 3.

TABLE 3

| Ethanol concentration (% by volume) | Amount of sodium bicarbonate added (% by weight) | Rottlerin extraction rate % | Relative ratio of extraction rate |
| --- | --- | --- | --- |
| 0 | 10 | 1.1 | 0.06 |
| 0 | 100 | 1.2 | 0.07 |

TABLE 3-continued

| Ethanol concentration (% by volume) | Amount of sodium bicarbonate added (% by weight) | Rottlerin extraction rate % | Relative ratio of extraction rate |
|---|---|---|---|
| 30 | 10 | 13.3 | 0.72 |
| 30 | 100 | 12.1 | 0.66 |
| 50 | 10 | 18.4 | 1.00 |
| 50 | 100 | 14.6 | 0.79 |

Explanations for Table 3: the extraction rate was only approximately 1% for the distilled water with an alcohol concentration of 0%. On the other hand, the relatively high extraction rate of 12.1 or 13.3% was achieved at the alcohol concentration of 30%. These correspond to approximately 70% of the extraction rate at the alcohol concentration of 50%.

EXAMPLE 7

Influence of pH on Rottlerin Extraction Efficiency

The influence of pH on rottlerin extraction efficiency was studied by performing extraction procedures at 80° C. for 1 hour with 50% ethanol at varying pH values according to the method of Example 2. Base components which are to be simultaneously added to change pH were, apart from sodium bicarbonate used in the Examples described above, sodium carbonate, disodium hydrogen phosphate (anhydrous), trisodium phosphate dodecahydrate (in Table 4, indicated by % calculated on the basis of the weight of its anhydrous form), and Atkins & Pantin's sodium carbonate/boric acid mixture solution (pH 8, 9, 10, 11; final ion strength: 50 mM). The types of the base components, the amounts of the base components added, the pH of the solvent used in extraction, the pH of a solution after extraction treatment, and rottlerin extraction rates are shown in Table 4. The Atkins & Pantin's sodium carbonate/boric acid mixture solution is a solution of an M/10 sodium carbonate aqueous solution (containing 10.6 g/L sodium carbonate) mixed with an M/10 boric acid/potassium chloride aqueous solution (containing 6.2 g/L boric acid and 7.45 g/L potassium chloride), and its pH can be adjusted to 8 by mixing them at a 1.12:8.80 ratio by capacity, to 9 by mixing them at a 3.70:6.30 ratio by capacity, to 10 by mixing them at a 7.09:2.91 ratio by capacity, and to 11 by mixing them at a 9.65:0.35 ratio by capacity. This mixture solution was simply shown as "buffer solution" in the table below.

TABLE 4

| Type | Amount added (% corresponds to % by weight with respect to raw material) | pH of 50% ethanol extraction solvent | pH of solution after extraction treatment | Rottlerin extraction rate % |
|---|---|---|---|---|
| Sodium bicarbonate | 0% | 6.6 | 5.2 | 0.4 |
| | 10% | 9.6 | 7.9 | 19.6 |
| | 30% | 9.6 | 8.2 | 19.4 |
| Sodium carbonate | 10% | 12.6 | 8.6 | 19.0 |
| | 30% | 12.7 | 10.6 | 14.3 |
| Disodium hydrogen phosphate | 10% | 10.0 | 6.6 | 5.9 |
| | 30% | 10.1 | 6.8 | 12.2 |
| Trisodium phosphate | 10% | 12.3 | 6.9 | 12.5 |
| | 30% | 12.5 | 8.6 | 20.0 |
| Buffer solution | pH 8.1, 50 mM | 9.8 | 5.9 | 4.2 |
| | pH 9.2, 50 mM | 10.7 | 7.2 | 17.7 |
| | pH 10.3, 50 mM | 11.6 | 8.3 | 18.0 |
| | pH 11.3, 50 mM | 12.3 | 8.9 | 15.5 |
| Sodium hydroxide | Adjusted to pH shown in the right | 11.5 | 4.9 | 0.3 |
| | | 12.4 | 5.2 | 0.5 |
| | | 13.3 | 6.3 | 6.1 |
| | | 14 | 6.3 | 6.5 |

Explanations for Table 4: the solution after extraction treatment exhibited a high rottlerin extraction rate at pH 7.0 to 11.0, particularly 7.0 to 9.0 (underlined boldfaces).

Figure 4:
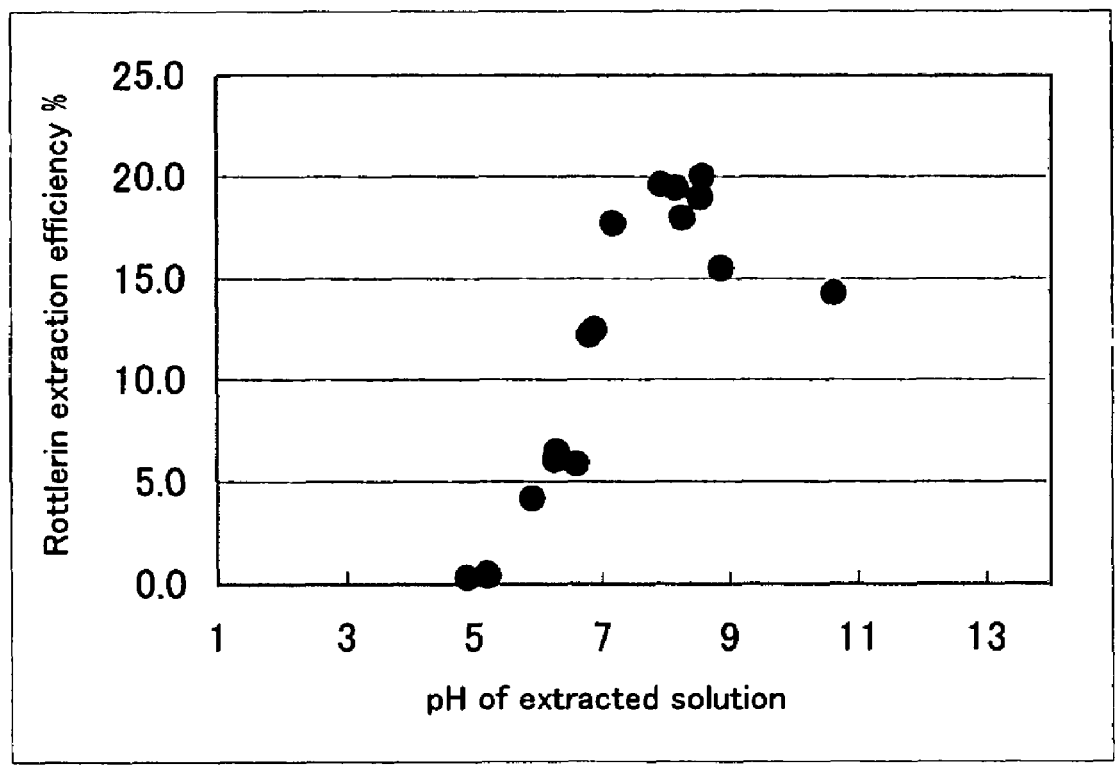
[FIG. 4]

The relationship between the pH of the solution after extraction treatment and the rottlerin extraction rate can clearly be read off from the accompanying drawing (FIG. 4).

The extraction rate obtained by the sodium bicarbonate-free 90% ethanol extraction was 19.4%, as shown in Example 2. A rottlerin extraction rate comparative to 80% or more of the value was achieved in the range from pH 7.0 to 9.0, while a rottlerin extraction rate corresponding to 70% or more thereof was achieved in the range from pH 7.0 to 11.0, demonstrating that the extraction rate is high at pH 7.0 or higher.

The invention claimed is:

1. A method for producing a *Mallotus philippinensis* dye composition comprising extracting a *Mallotus philippinensis* plant body with an alcohol-containing aqueous solvent in the presence of a base component, wherein the *Mallotus philippinensis* plant body is a powdered kamala.

2. The production method according to claim 1, wherein the dye composition contains rottlerin as a dye component.

3. The production method according to claim 1, wherein the solvent has an alcohol concentration of 30 to 90% by volume.

4. The production method according to claim 3, wherein the solvent has an alcohol concentration of 30 to 70% by volume.

5. The production method according to claim 1, wherein the base component is at least one base selected from the group consisting of ammonium carbonate, potassium carbonate, sodium carbonate, sodium bicarbonate, tripotassium phosphate, diammonium hydrogen phosphate, dipotassium hydrogen phosphate, disodium hydrogen phosphate, trisodium phosphate, potassium hydroxide, and sodium hydroxide.

6. The production method according to claim 5, wherein the base component is at least one base selected from the group consisting of sodium bicarbonate, sodium carbonate, and trisodium phosphate.

7. The production method according to claim 6, wherein the amount of the base component used is 10 to 300% by weight with respect to the amount of the *Mallotus philippinensis* plant body.

8. The production method according to claim 7, wherein the amount of the base component used is 10 to 30% by weight with respect to the amount of the *Mallotus philippinensis* plant body.

9. The production method according to claim 1, wherein the amount of the solvent used in the extraction is 5 to 20 times by weight larger-than that of the *Mallotus philippinensis* plant body.

10. The production method according to claim 1, wherein the extraction is performed under conditions where the solvent in contact with the plant body has a pH of 7.0 or higher.

11. The production method according to claim 10, wherein the extraction is performed under conditions where the solvent in contact with the plant body has a pH of 7.0 to 11.

12. The production method according to claim 11, wherein the extraction is performed under conditions where the solvent in contact with the plant body has a pH of 7.0 to 9.0.

13. The production method according to claim 1, wherein the temperature of the solvent during the extraction is room temperature to reflux temperature.

14. The production method according to claim 13, wherein the temperature of the solvent during the extraction is 50 to 80° C.

15. A water-soluble *Mallotus philippinensis* dye composition produced by a production method according to claim 1, wherein rottlerin contained in the composition has a water solubility of 250 μg/mL-12,750 μg/mL.

16. The dye composition according to claim 15, wherein the dye composition is used as a coloring agent and/or a preservative agent in foods, drinks, or cosmetics, or used as an anthelmintic.

* * * * *